(12) United States Patent
Ishihara et al.

(10) Patent No.: US 12,310,662 B2
(45) Date of Patent: May 27, 2025

(54) MEASURING METHOD FOR MEASURING ROTATION CHARACTERISTIC OF EYEBALL OF SUBJECT AND SETTING METHOD FOR PROGRESSIVE POWER LENS

(71) Applicant: HOYA LENS THAILAND LTD., Pathumthani (TH)

(72) Inventors: Nagisa Ishihara, Tokyo (JP); Eiichiro Yamaguchi, Tokyo (JP); Ayumu Ito, Tokyo (JP); Toshiaki Sonehara, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 901 days.

(21) Appl. No.: 17/599,795

(22) PCT Filed: Mar. 26, 2020

(86) PCT No.: PCT/JP2020/013664
§ 371 (c)(1),
(2) Date: Sep. 29, 2021

(87) PCT Pub. No.: WO2020/203645
PCT Pub. Date: Oct. 8, 2020

(65) Prior Publication Data
US 2022/0183554 A1 Jun. 16, 2022

(30) Foreign Application Priority Data
Mar. 29, 2019 (JP) ................................ 2019-066410

(51) Int. Cl.
*A61B 3/113* (2006.01)
*A61B 3/00* (2006.01)
(Continued)

(52) U.S. Cl.
CPC .............. *A61B 3/113* (2013.01); *A61B 3/005* (2013.01); *A61B 3/14* (2013.01); *G02C 7/027* (2013.01); *G02C 7/061* (2013.01); *G06F 3/147* (2013.01)

(58) Field of Classification Search
CPC ..... A61B 3/0041; A61B 3/005; A61B 3/0091; A61B 3/028; A61B 3/032; A61B 3/14;
(Continued)

(56) References Cited

U.S. PATENT DOCUMENTS

| | | |
|---|---|---|
| 6,199,983 B1 | 3/2001 | Kato et al. |
| 2016/0011437 A1 | 1/2016 | Nishimura et al. |

(Continued)

FOREIGN PATENT DOCUMENTS

| | | |
|---|---|---|
| CN | 105026989 A | 11/2015 |
| CN | 107450720 A | 12/2017 |

(Continued)

OTHER PUBLICATIONS

Mar. 23, 2022 extended Search Report issued in European Patent Application No. 20782205.7.
(Continued)

*Primary Examiner* — Jack Dinh
(74) *Attorney, Agent, or Firm* — Oliff PLC

(57) ABSTRACT

A measuring method for measuring rotation characteristics of an eyeball of a subject includes: showing display information on a display screen, at a position separated from a reference position, the display screen being shown in front of the eyeball of the subject by a display device that is secured to a head of the subject, the reference position being where a front line of sight of the eyeball of the subject who looks forward straightly, crosses the display screen; changing a direction of a line of sight from the eyeball to the display information by switching the display information to (Continued)

other contents while changing a displayed position of the display information; and judging whether the subject can recognize the contents of the display information at the changed position, to measure the rotation characteristics of the eyeball.

20 Claims, 4 Drawing Sheets

(51) Int. Cl.
*A61B 3/14* (2006.01)
*G02C 7/02* (2006.01)
*G02C 7/06* (2006.01)
*G06F 3/147* (2006.01)

(58) Field of Classification Search
CPC ......... A61B 3/115; A61B 3/152; G02C 7/027; G02C 7/061; G02C 7/065; G06F 3/013; G06F 3/147
See application file for complete search history.

(56) References Cited

U.S. PATENT DOCUMENTS

| | | |
|---|---|---|
| 2017/0171539 A1 | 6/2017 | Inomata |
| 2017/0344112 A1 | 11/2017 | Wilson et al. |

FOREIGN PATENT DOCUMENTS

| | | |
|---|---|---|
| EP | 0880046 A1 | 11/1998 |
| EP | 2 899 585 A1 | 7/2015 |
| EP | 2 963 483 A1 | 1/2016 |
| JP | H10-161800 A | 6/1998 |
| JP | 2006-163441 A | 6/2006 |
| JP | 2017-215928 A | 12/2017 |
| JP | 6332392 B2 | 5/2018 |
| KR | 10-2017-0135762 A | 12/2017 |
| WO | 1998/016862 A1 | 4/1998 |
| WO | 2014/133166 A1 | 9/2014 |
| WO | 2016/167091 A1 | 10/2016 |
| WO | 2019/013563 A1 | 1/2019 |

OTHER PUBLICATIONS

Jun. 16, 2020 International Search Report issued in International Patent Application No. PCT/JP2020/013664.

MEASURING METHOD FOR MEASURING ROTATION CHARACTERISTIC OF EYEBALL OF SUBJECT AND SETTING METHOD FOR PROGRESSIVE POWER LENS

FIELD

The present invention relates to a measuring method for measuring rotation characteristics of an eyeball of a subject and a designing method for designing a progressive power lens by using measurement result of the measuring method.

BACKGROUND

Eyeglass lenses using progressive power lenses are publicly known. The progressive power lens has regions of a distance vision part for distance viewing, a near vision part for near viewing, and an intermediate vision part positioned between the distance vision part and the near vision part, and the progressive power lens changes in refractive power between the distance vision part and the near vision part.

The progressive power lens is designed by determining a spherical power at the distance measurement position, a cylindrical power and an addition power, in accordance with the distance power, astigmatism power, and near power of a person who will purchase eyeglasses (hereinafter simply called a "purchaser").

A progressive power lens is individually designed so as to be suitable for an eye of each purchaser by adjusting a spherical power, a cylindrical power, and an addition power. For a progressive power lens more suitable for an eye of a purchaser, it is more preferable to design a progressive power lens by determining rotation characteristics of an eyeball, which differ depending on the purchaser, and using the rotation characteristics in addition to a spherical power, a cylindrical power, and an addition power.

A technique using a line-of-sight information correction device is known as a method for measuring rotation characteristics of an eyeball (Patent literature 1). The line-of-sight information correction device is able to measure correct line-of-sight information although an optical tool, such as eyeglass lenses, is used. This technique involves measuring line-of-sight information of a purchaser of eyeglass lenses and using the measurement result to design a lens suitable for a line of sight of the purchaser.

CITATION LIST

Patent Literature

Patent literature 1: Japanese Patent No. 6332392

BRIEF SUMMARY

Technical Problem

The line-of-sight information correction device uses an eyeball photographing camera that is fixed to a headband mounted on the head of a subject, who is a purchaser. The camera photographs an eyeball through an eyeglass lens, whereby line-of-sight information of the eyeball is obtained. The line-of-sight information correction device corrects the obtained line-of-sight information with the use of a result of tracking a light ray, which is performed on the eyeglass lens in advance, and optical information relating to optical refraction of the eyeglass lens. Thus, correct line-of-sight information is measured. Rotation characteristics of the eyeball can be examined by using this line-of-sight information.

However, the line-of-sight information of an eyeball is sometimes not correctly obtained due to the following reason. The line-of-sight information correction device photographs line-of-sight information by using the eyeball photographing camera, which is fixed to the headband mounted on the head of a subject, and the subject may look at a target fixation point by slightly inclining or moving the subject's head or body. In particular, for a line of sight in which rotation characteristics of an eyeball, or more specifically, rotation of an eyeball, is close to limit, the direction of the line of sight is often moderated by slightly inclining or moving the head or the body.

This makes it difficult to measure rotation characteristics of an eyeball with high accuracy.

In view of this, an object of the present invention is to provide a measuring method for measuring rotation characteristics of an eyeball with high accuracy compared with a conventional method and to provide a designing method for designing a progressive power lens by using measurement result of the measuring method.

Solution to Problem

An embodiment of this disclosure is a measuring method for measuring rotation characteristics of an eyeball of a subject. The measuring method includes:
  showing display information on a display screen, at a position separated from a reference position, the display screen being shown in front of the eyeball of the subject by a display device that is secured to a head of the subject, the reference position being where a front line of sight of the eyeball of the subject who looks forward straightly, crosses the display screen;
  changing a direction of a line of sight from the eyeball to the display information by switching the display information to other contents while changing a displayed position of the display information; and
  judging whether the subject can recognize the contents of the display information at the changed position, to measure the rotation characteristics of the eyeball.

Preferably, the changing a direction of the line of sight may include moving the displayed position at least along an up-down direction of the display screen relative to the reference position.

Preferably, timing to switch the displayed positions and the contents may be adjusted so that at least one of two pieces of information is obtained as the rotation characteristics of the eyeball. The one of the two pieces of information is a limit angle of a line of sight directed to a lowest side relative to the front line of sight, in a range in which the display information is determined to be able to be recognized by rotating the eyeball downward. The other of the two pieces of information is a time period to maintain the eyeball in a state in which the display information is determined to be able to be recognized while the line of sight is directed downward by a predetermined angle relative to the front line of sight.

Preferably, the changing a direction of the line of sight may include repeatedly moving the displayed position after the contents of the display information are repeatedly switched to other contents by a predetermined number of times while the displayed position is fixed for a predetermined time.

Preferably, the displayed position may become separated from the reference position in one direction in the display screen each time the displayed position is moved.

Preferably, the changing a direction of the line of sight may include repeatedly moving the displayed position in such a manner that the displayed position becomes separated from the reference position in one direction in the display screen each time the contents are switched.

Preferably, the displayed position in a direction orthogonal to the one direction may be in a predetermined range and may be changed in this range at the time of switching the contents or moving the displayed position in the one direction.

Preferably, the showing display information on the display screen may include adjusting at least one of the reference position and the displayed position as seen from the subject, with a use of an optical system provided between the display screen and the eyeball.

Preferably, the optical system may include at least one prism.

Then, the displayed position of the display information in the display screen may be preferably adjusted in accordance with refractive characteristics of the prism.

Preferably, the judging whether the subject can recognize the contents of the display information may include determining whether a response to the contents of the display information by the subject coincides with the contents.

Other embodiment of the present disclosure is a designing method for a progressive power lens suitable for rotation characteristics of an eyeball of a subject, the progressive power lens having regions of a distance vision part for distance viewing, a near vision part for near viewing, and an intermediate vision part positioned between the distance vision part and the near vision part, the progressive power lens changing in refractive power between the distance vision part and the near vision part. The designing method includes:

showing display information on a display screen, at a position separated from a reference position, the display screen being shown in front of the eyeball of the subject by a display device that is secured to a head of the subject, the reference position being where a front line of sight of the eyeball of the subject who looks forward straightly, crosses the display screen;

changing a direction of a line of sight from the eyeball to the display information by switching the display information to other contents while changing a displayed position of the display information;

judging whether the subject can recognize the contents of the display information at the changed position, to measure the rotation characteristics of the eyeball;

adjusting timing to switch the displayed positions and the contents so that at least one of two pieces of information is obtained as the rotation characteristics of the eyeball, the one of the two pieces of information being a limit angle of a line of sight directed to a lowest side relative to the front line of sight, in a range in which the display information is determined to be able to be recognized by rotating the eyeball downward, the other of the two pieces of information being a time period to maintain the eyeball in a state in which the display information is determined to be able to be recognized while the line of sight is directed downward by a predetermined angle relative to the front line of sight; and determining a progressive corridor length or a shape of a refractive power curve along which refractive power changes, in the progressive power lens, on a basis of the measured information of the limit angle of the line of sight or the measured information of the time period to maintain the eyeball.

Advantageous Effects

The measuring method for measuring rotation characteristics of an eyeball of a subject enables measuring rotation characteristics of an eyeball with high accuracy compared with a conventional method. As a result, it is possible to design a progressive power lens suitable for rotation characteristics of a measured eyeball.

DETAILED DESCRIPTION

The following describes a measuring method for measuring rotation characteristics of an eyeball of a subject and a designing method for a progressive power lens according to an embodiment of the present invention, based on the attached drawings.

Figure 1:
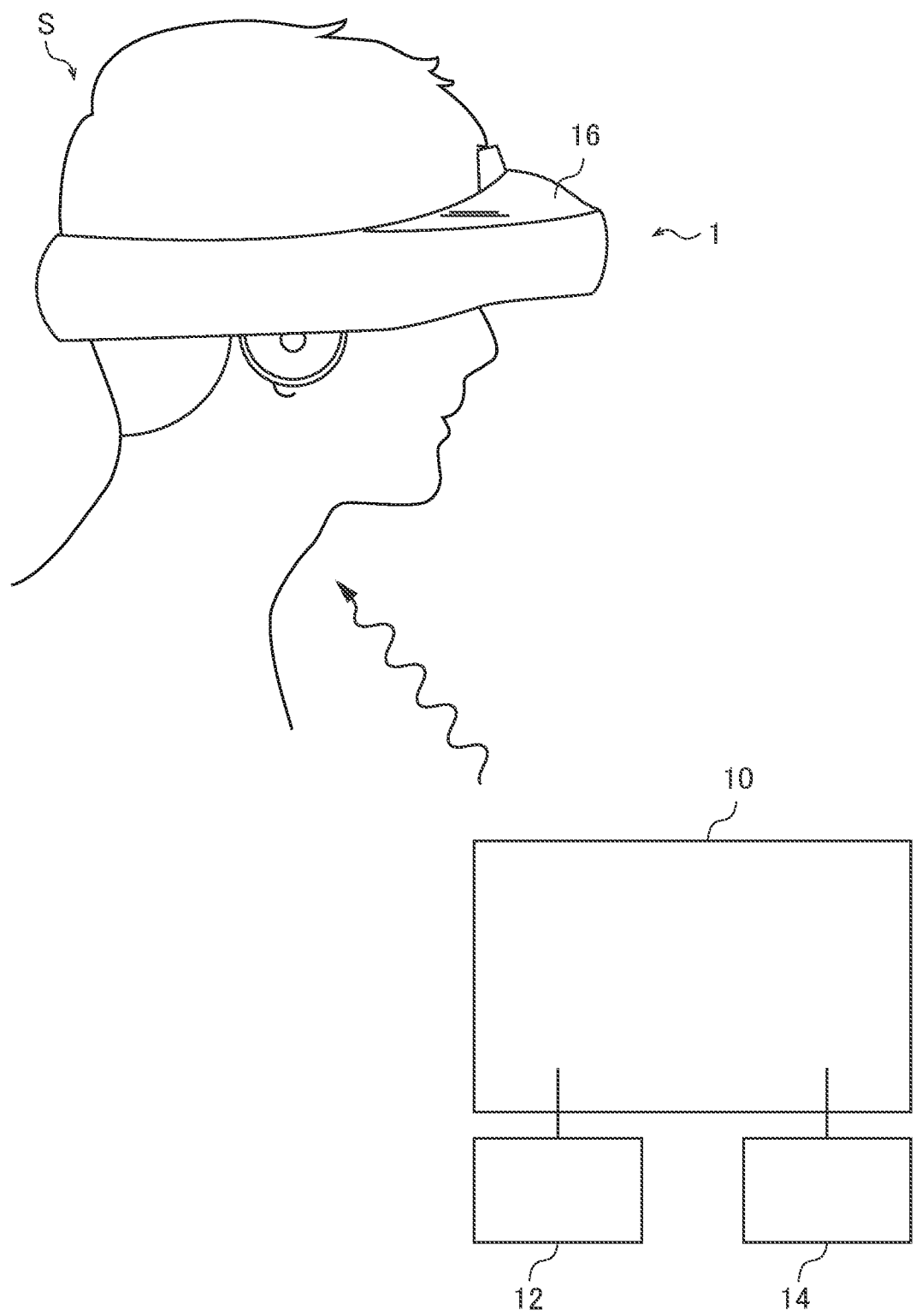
FIG. 1 shows a schematic configuration of a measurement system that implements a measuring method for measuring rotation characteristics of an eyeball of a subject according to an embodiment.

FIG. 1 shows a schematic configuration of a measurement system 1 that implements a measuring method for measuring rotation characteristics of an eyeball of a subject according to one embodiment.

The measurement system 1 primarily includes a computer 10 and a head-mounted display 16.

The head-mounted display 16 is a display device that shows a display screen in front of an eyeball of a subject "S" in a state in which it is secured to the head of the subject "S". FIG. 1 shows an example of using the head-mounted display 16 as a display device, but any display device can be used on the condition that it shows a display screen in front of an eyeball of the subject "S" in a state of being secured to the head of the subject "S".

The computer 10 is connected to an input operation system 12, such as a mouse and a keyboard, and is also connected to a monitor 14. The monitor 14 displays information such as a result of measuring rotation characteristics of an eyeball, and contents and a displayed position of display information shown on the display screen of the head-mounted display 16, which will be described later. Moreover, a measurement condition setting screen is also displayed to allow setting details of a procedure of the measuring method for measuring rotation characteristics of an eyeball.

The computer 10 includes a memory, which is not shown in the drawing, and measurement software for measuring rotation characteristics of an eyeball is recorded in the memory. The computer 10 reads and drives this measurement software and thereby makes the head-mounted display 16 show display information on the display screen.

Specifically, the head-mounted display 16 shows display information at a position separated from a reference position, on the display screen. The reference position is where a front line of sight of an eyeball of the subject "S" who looks forward straightly in accordance with an instruction of the computer 10, crosses the display screen. The display information is information that can be recognized by the subject "S" who looks forward straightly and includes information such as a character, a symbol, or a mark, or color information. The display information is wirelessly transmitted from the computer 10.

Moreover, the head-mounted display 16 switches the display information to other contents while changing the displayed position of the display information, whereby the direction of a line of sight of the subject "S" from the eyeball of the subject "S" to the display information is changed.

At this time, the subject "S" speaks the contents of the display information to an operator of the computer 10. The operator inputs the contents of the display information hearing from the subject "S", into the computer 10 via the input operation system 12.

The computer 10 determines whether the display information shown on the head-mounted display 16 and the input display information coincide with each other, to judge whether the subject "S" can recognize the contents of the display information at the changed position.

This reveals the range of the displayed position of the display information that can be recognized by the subject "S", and this range is used as a result of measuring rotation characteristics of the eyeball.

The contents of the display information shown on the display screen change at a constant time interval. In consideration of this, whether the subject "S" could recognize may be judged by determining whether a percentage of correct answers for multiple contents exceeds a predetermined rate. Alternatively, it may be judged that the subject "S" cannot recognize, in a case in which the input display information does not coincide with the display information shown on the head-mounted display 16 even once.

Figure 2A:
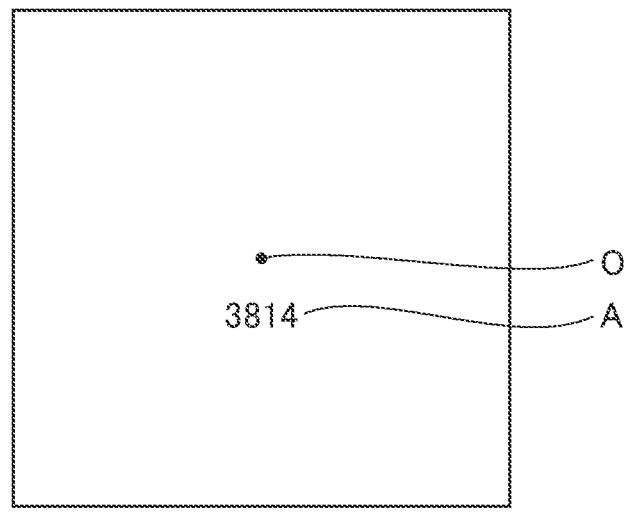
FIGS. 2A and 2B show examples of display information that is shown on a display screen of a display device of the measurement system of the embodiment.
Figure 2B:
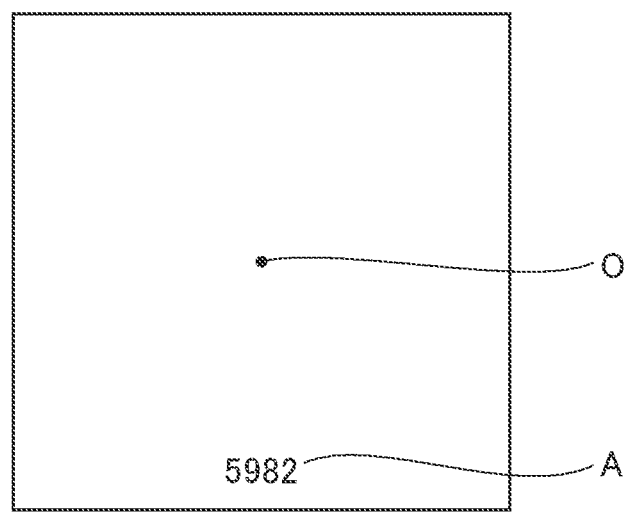

FIGS. 2A and 2B show examples of the display information shown on the display screen of the head-mounted display 16.

FIG. 2A shows a symbol "3814" as display information "A" at a position separated from a reference position "O". FIG. 2B shows a symbol "5982" as display information "A" at a position separated from the display information "A" in FIG. 2A as seen from the reference position "O". In this manner, the displayed position and the contents of the display information "A" are changed in the head-mounted display 16. The subject "S" responds to the contents of such display information "A", that is, for example, speaks the contents to an operator.

Note that the head-mounted display 16 may show display information "A" having the same contents at the same displayed positions on both of display screens corresponding to both eyes, whereby overall rotation characteristics of the both eyes may be measured. Alternatively, the head-mounted display 16 may show display information "A" at a predetermined displayed position only on a display screen corresponding to one eye, whereby rotation characteristics may be measured per eye.

In this manner, the head-mounted display 16 switches the contents of the display information to other contents while changing the displayed position of the display information at a position separated from the reference position. This enables efficiently measuring rotation characteristics of an eyeball. Moreover, the head-mounted display 16 is secured to the head of the subject "S", and therefore, the positional relationship between an eye and the display information does not vary, unlike a conventional manner. Thus, it is possible to measure rotation characteristics of an eyeball with high accuracy, compared with a conventional technique.

In the above-described embodiment, the coincidence between the contents of the display information "A" shown on the head-mounted display 16 and the contents of the display information "A" recognized by the subject "S" is determined as follows. The subject "S" speaks the contents to an operator, the operator then inputs the contents of the display information "A" into the computer 10 via the input operation system 12, and the input contents are used in determination. However, the subject "S" may directly input by using the input operation system 12. Alternatively, instead of inputting the contents of the display information "A" recognized by the subject "S" via the input operation system 12, a voice of the subject "S" responding to the contents of the display information "A" may be input into the computer 10 through a microphone. In this case, the computer 10 may distinguish the contents of the display information "A" spoken by the subject "S", among the voice signal of the input voice. Then, the computer 10 may determine the coincidence between the distinguished result and the contents of the display information "A" shown on the head-mounted display 16.

Rotation characteristics of an eyeball include a rotation characteristic in a right-left direction as well as a rotation characteristic in an up-down direction, and also include a rotation characteristic in a direction tilted in an up-down direction and a right-left direction by a certain angle relative to a front view.

Nevertheless, in one embodiment, it is preferable to move the displayed position at least along an up-down direction of the display screen relative to the reference position, in order to change the direction of a line of sight of the subject "S". In general living environment, in most cases, a line of sight is lowered in order to look at a close object on a near side, and a line of sight is raised in order to look at a distant object on a far side, relative to an object that is viewed with a front line of sight. In consideration of this, measuring rotation characteristics in the up-down direction of a line of sight is preferable in terms of individually designing an eyeglass lens in accordance with rotation characteristics of the subject "S".

Rotation of an eyeball mainly depends on muscle characteristics of extraocular muscles around an eyeball. The muscle characteristics are characterized by the maximum muscular strength and a time period to maintain a certain muscular strength. Thus, rotation characteristics of an eyeball are also characterized by a rotation limit range of an eye and information relating to a time period to maintain a line of sight in a certain direction relative to a direction of a front view.

For this reason, in one embodiment, it is preferable to adjust timing to switch the displayed positions and the contents of the display information "A" so that at least one of the following two pieces of information will be obtained as rotation characteristics of an eyeball. One of the two pieces of information is a limit angle of a line of sight of the subject "S" directed to a lowest side relative to a front line of sight of the eyeball, in a range in which the display information "A" is determined to be able to be recognized by rotating the eyeball downward. The other is a time period to maintain the eyeball in a state in which the display information "A" is determined to be able to be recognized while a line of sight is directed downward by a predetermined angle relative to a front line of sight of the subject "S".

The direction of a line of sight of the subject "S" is preferably changed by repeatedly moving the displayed position after the contents of the display information "A" are repeatedly switched to other contents by a predetermined number of times while the displayed position is fixed for a predetermined time. In this case, the subject "S" speaks the contents to an operator each time the contents of the display information "A" are switched while the displayed position is fixed for a predetermined time. Meanwhile, the responses may be consecutively wrong after some time has passed. In such a situation, the time period while the responses are consecutively correct can be obtained as the information of the time period to maintain the eyeball.

The subject "S" speaks the contents to an operator each time the contents of the display information "A" are changed while the displayed position is maintained. At this time, for example, a rotation ability index "P" may be calculated as a rotation characteristic of the eyeball. The rotation ability index "P" is represented by a function P=f(q, t, θ) using a percentage "q" of correct answers of the subject "S", a measured response time period "t" until a response is provided after the contents of the display information "A" are switched, and an angle θ (angle relative to a front view) of the direction of a line of sight. An example of the function "f" may be expressed by the following formula.

$$P=f(q,t,\theta)=(q\times\alpha)\times(1/(t\times\beta))\times(\theta\times\gamma)$$

(where α, β, and γ are predetermined coefficients)

In one embodiment, it is preferable that the displayed position of the display information "A" become separated from the reference position "O" in one direction in the display screen each time the displayed position is moved. The display information "A" is shown in such a manner that the displayed position is gradually separated from the reference position "O", whereby rotation characteristics can be measured efficiently.

In one embodiment, the direction of a line of sight of the subject "S" is preferably changed by repeatedly moving the displayed position in such a manner that it becomes separated from the reference position "O" in one direction in the display screen, each time the contents of the display information "A" are switched. For example, the information of a limit angle of a line of sight directed to a lowest side relative to a front line of sight of an eyeball, in a range in which the display information "A" is determined to be able to be recognized, is obtained as a rotation characteristic. In this case, it is not necessary to measure a time period to maintain the eyeball directed to a fixed direction. Thus, the rotation characteristic can be efficiently measured by repeatedly moving the displayed position in such a manner that it becomes separated from the reference position "O" each time the contents of the display information "A" are switched.

In one embodiment, it is preferable that the position of the display information "A" in a direction orthogonal to the direction of moving the displayed position of the display information "A" be in a predetermined range and be changed in this range at the time of switching the contents of the display information "A" or moving the displayed position. In one example in which the displayed position of the display information "A" is moved downward of the reference position "O", the position in the right-left direction of the display information "A" is changed in a predetermined range. This makes an eye move in the right-left direction, compared with a case of showing the display information "A" at the same position in the right-left direction each time. Thus, rotation characteristics of the eye in the downward direction are effectively measured while a moderate stimulus is applied to the eye in the right-left direction. On the other hand, it is undesirable that the subject "S" expect the display information "A" to be shown at the same position in the right-left direction on a lower side and concentrate on the expected position, in terms of accurate measurement of rotation characteristics.

In one embodiment, the display information "A" is preferably shown on the display screen of the head-mounted display 16 by adjusting at least one of the reference position "O" and the displayed position of the display information "A" as seen from the subject "S", with the use of an optical system provided between the display screen and the eyeball.

At least one of the reference position "O" and the displayed position of the display information "A" as seen from the subject "S" is adjusted by using the optical system, whereby rotation characteristics, in particular, a limit range of rotation, can be measured although the display area of the display screen of the head-mounted display 16 is limited. Herein, the optical system includes a mirror, a lens, and a prism. In one example, the mirror may be used in order to change the direction of a line of sight or to adjust an optical path length from the display screen to an eyeball.

On the other hand, the subject "S" may correct the subject's eyes by using eyeglasses or the like. In this case, the eyeglass lenses function as a part of the optical system. That is, the subject "S" may undergo the measurement while wearing eyeglasses. Under these conditions, the direction of a line of sight to the display information "A" is determined by the displayed position and a prismatic effect of the eyeglass lens. In this case, the displayed position of the display information "A" is preferably set on the basis of refractive characteristics based on the prismatic effect of the eyeglass lens, so that the direction of a line of sight, in which the subject "S" looks at the display information "A" through the eyeglass lens, will be a predetermined direction. That is, it is preferable that the computer 10 set the displayed position of the display information "A" so that a line of sight will be directed to a set direction in response to reception of input information of the refractive characteristics of the eyeglass lens. In addition, the eyeglass lens is required to have known prism characteristics, and therefore, the subject "S" preferably undergoes the measurement while wearing eyeglass lenses that are selected from multiple eyeglass lenses having known prism characteristics, which are prepared beforehand.

Figure 3:
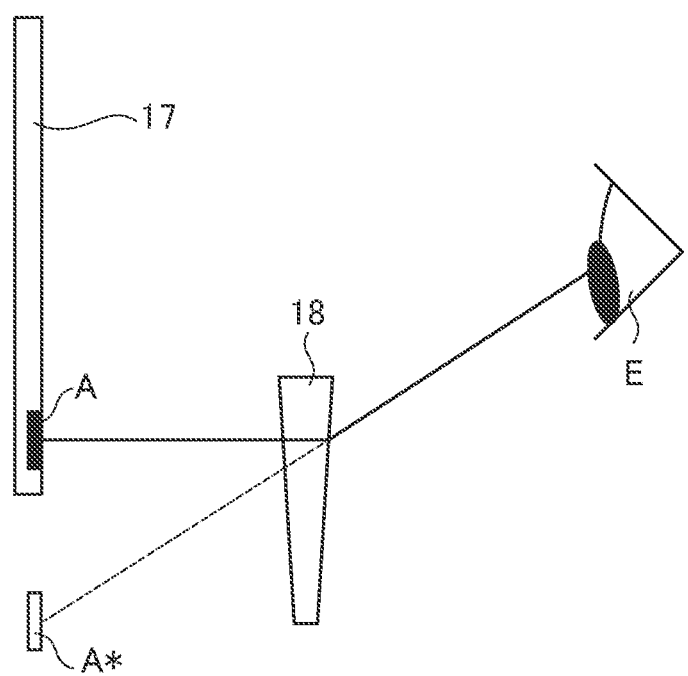
FIG. 3 is an explanatory drawing of an optical system used in one embodiment.

In one embodiment, the optical system preferably includes at least one prism. A line of sight of an eye can be directed upward, downward, right, and left by approximately 45 to 50 degrees in terms of a tilt angle relative to a front view. On the other hand, an angle of a line of sight looking at the most distant position in the up-down direction of the reference position "O" is 40 degrees at most relative to a front view, in the display screen of the head-mounted display 16. For this reason, the display screen of the head-mounted display 16 does not have an area enough to measure a rotation limit range of an eye. In view of this, the optical system preferably includes at least one prism. FIG. 3 is an explanatory drawing of an optical system used in one embodiment.

FIG. 3 shows display information "A" shown on a display screen 17. A prism 18 is provided between the display screen 17 and an eye "E", and therefore, the subject "S" sees display information "A*" as display information "A", at a position lower than the displayed position of the display information "A". That is, although the display information "A" is at the lowest position in the display screen 17, the line of sight is directed to the position outside the display screen 17. In this manner, it is preferable that the optical system include at least one prism because rotation characteristics of an eye can be measured although the head-mounted display 16 has a limited display range.

Figure 4:
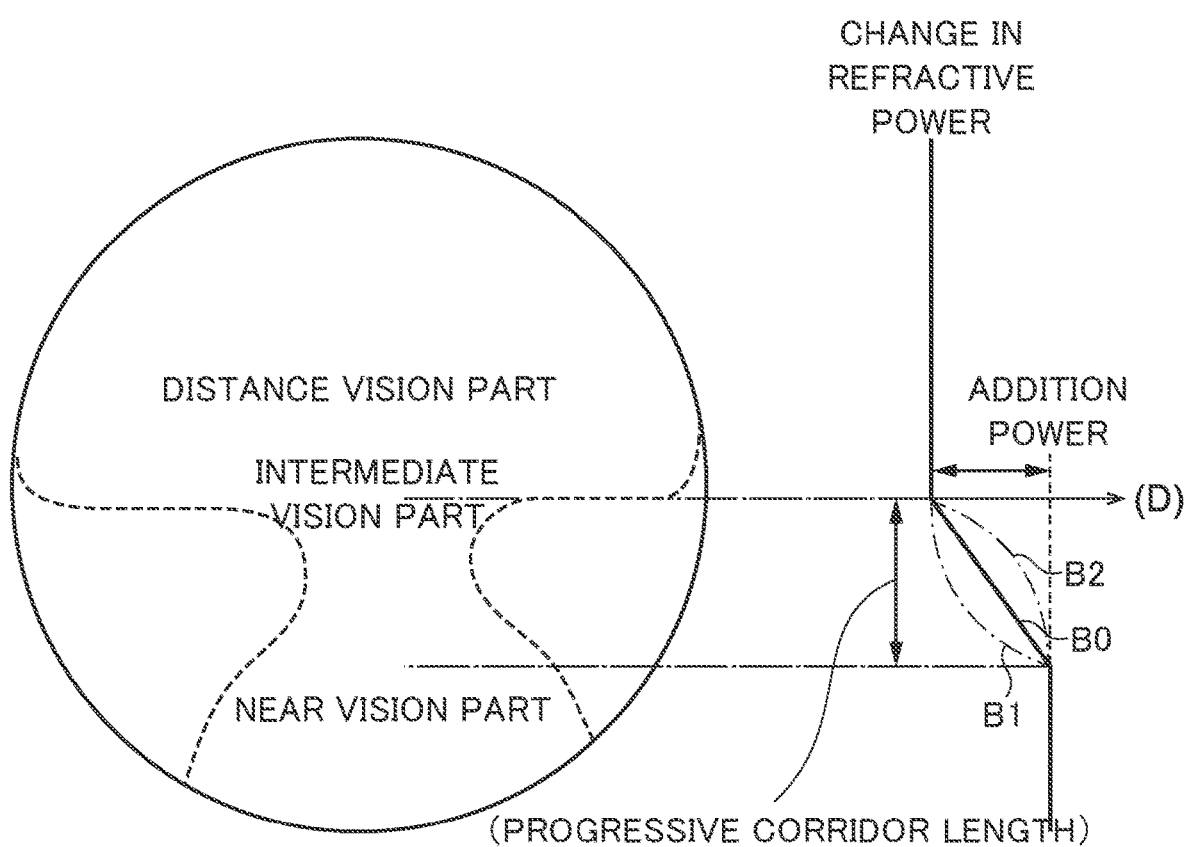
FIG. 4 schematically shows a progressive power lens.

Such a result of the rotation characteristics can be effectively used in designing a progressive power lens among eyeglass lenses. FIG. 4 schematically shows a progressive power lens in a state of a circle-shaped lens substrate that is not subjected to edging for providing a shape corresponding to the shape of an eyeglass frame.

As shown in FIG. 4, the progressive power lens is an eyeglass lens that has regions of a distance vision part for distance viewing, a near vision part for near viewing, and an intermediate vision part positioned between the distance vision part and the near vision part, and the progressive power lens changes in refractive power between the distance vision part and the near vision part.

In designing a progressive power lens suitable for rotation characteristics of an eyeball of a person who will purchase eyeglasses, the person is assumed as a subject "S", and the rotation characteristics of the eyeball of the subject "S" are measured by using the measurement system 1.

This measurement provides information of a limit angle of a line of sight of the subject "S" or information of a time period to maintain the eyeball. On the basis of this information, a progressive corridor length or a shape of a refractive power curve along which refractive power changes, in a progressive power lens, is determined.

The progressive corridor length is a length of a part in which the refractive power continuously changes from the intermediate vision part to the near vision part. In one embodiment, the refractive power curve is set in such a manner that refractive power in the progressive corridor length is linearly varied as in a straight line B0 or is non-linearly varied as in a curve B1 or B2.

In one example, a result of measuring rotation characteristics of a line of sight of the subject "S" shows that a downward-rotation maintained angle (maximum angle at which downward rotation is maintained for a time period satisfying a predetermined range) of an eyeball is small. In this case, the progressive corridor length is set to be short. Conversely, in a case in which information of a limit angle of a line of sight of the subject "S" shows that the downward-rotation maintained angle of the eyeball is large, the progressive corridor length is set to be long. In addition, the refractive power curve may be set so as to have the curve B1 or B2 in accordance with the measurement result.

The time period to maintain an eyeball may vary although the information of a limit angle of a line of sight is the same. In one example in which the time period to maintain an eyeball is short, in order to enable viewing while holding a line of sight for a certain time period without greatly moving the line of sight downward, the dioptric power at the intermediate vision part is preferably made higher than that in the straight line B0, as in the curve B2.

In the case of measuring overall rotation characteristics of both eyes in order to design progressive power lenses suitable for the rotation characteristics of the eyes, the measurement result is reflected in progressive power lenses for right and left eyes. In measuring rotation characteristics of right and left eyes separately, the measurement results may differ from each other. In this case, the measurement results of the both eyes may be respectively reflected in the designs of corresponding progressive power lenses, or an average of the measurement results of the rotation characteristics of the both eyes may be reflected in the designs of corresponding progressive power lenses.

The measuring method for measuring rotation characteristics of an eyeball of a subject and a designing method for a progressive power lens of the present invention are detailed above. However, the present invention is not limited to the foregoing embodiments, and of course, various modifications and alterations may be made without departing from the gist of the present invention.

REFERENCE SIGNS LIST

1 measurement system
10 computer
12 input operation system
14 monitor
16 head-mounted display
17 display screen
18 prism

The invention claimed is:

1. A measuring method for measuring rotation characteristics of an eyeball of a subject, the measuring method comprising:
   showing display information on a display screen, at a position separated from a reference position, the display screen being shown in front of the eyeball of the subject by a display device that is secured to a head of the subject, the reference position being where a front line of sight of the eyeball of the subject who looks forward straightly, crosses the display screen;
   changing a direction of a line of sight from the eyeball to the display information by switching the display information to other contents while changing a displayed position of the display information; and
   judging whether the subject can recognize the contents of the display information at the changed position, to measure the rotation characteristics of the eyeball.

2. The measuring method according to claim 1, wherein the changing a direction of the line of sight includes moving the displayed position at least along an up-down direction of the display screen relative to the reference position.

3. The measuring method according to claim 2, wherein timing to switch the displayed positions and the contents is adjusted so that at least one of two pieces of information is obtained as the rotation characteristics of the eyeball, the one of the two pieces of information being a limit angle of a line of sight directed to a lowest side relative to the front line of sight, in a range in which the display information is determined to be able to be recognized by rotating the eyeball downward, and the other of the two pieces of information being a time period to maintain the eyeball in a state in which the display information is determined to be able to be recognized while the line of sight is directed downward by a predetermined angle relative to the front line of sight.

4. The measuring method according to claim 2, wherein the changing a direction of the line of sight includes repeatedly moving the displayed position after the contents of the display information are repeatedly switched to other contents by a predetermined number of times while the displayed position is fixed for a predetermined time.

5. The measuring method according to claim 2, wherein the changing a direction of the line of sight includes repeatedly moving the displayed position in such a manner that the displayed position becomes separated from the reference position in one direction in the display screen each time the contents are switched.

6. The measuring method according to claim 2, wherein the showing display information on the display screen includes adjusting at least one of the reference position and the displayed position as seen from the subject, with a use of an optical system provided between the display screen and the eyeball.

7. The measuring method according to claim 1, wherein timing to switch the displayed positions and the contents is adjusted so that at least one of two pieces of information is obtained as the rotation characteristics of the eyeball, the one of the two pieces of information being a limit angle of a line of sight directed to a lowest side relative to the front line of sight, in a range in which the display information is determined to be able to be recognized by rotating the eyeball downward, and the other of the two pieces of information being a time period to maintain the eyeball in a state in which the display information is determined to be able to be recognized while the line of sight is directed downward by a predetermined angle relative to the front line of sight.

8. The measuring method according to claim 7, wherein the changing a direction of the line of sight includes repeatedly moving the displayed position after the contents of the display information are repeatedly switched to other contents by a predetermined number of times while the displayed position is fixed for a predetermined time.

9. The measuring method according to claim 7, wherein the changing a direction of the line of sight includes repeatedly moving the displayed position in such a manner that the displayed position becomes separated from the reference position in one direction in the display screen each time the contents are switched.

10. The measuring method according to claim 7, wherein the showing display information on the display screen includes adjusting at least one of the reference position and the displayed position as seen from the subject, with a use of an optical system provided between the display screen and the eyeball.

11. The measuring method according to claim 1, wherein the changing a direction of the line of sight includes repeatedly moving the displayed position after the contents of the display information are repeatedly switched to other contents by a predetermined number of times while the displayed position is fixed for a predetermined time.

12. The measuring method according to claim 11, wherein the displayed position becomes separated from the reference position in one direction in the display screen each time the displayed position is moved.

13. The measuring method according to claim 12, wherein the displayed position in a direction orthogonal to the one direction is in a predetermined range and is changed in this range at the time of switching the contents or moving the displayed position in the one direction.

14. The measuring method according to claim 1, wherein the changing a direction of the line of sight includes repeatedly moving the displayed position in such a manner that the displayed position becomes separated from the reference position in one direction in the display screen each time the contents are switched.

15. The measuring method according to claim 14, wherein the displayed position in a direction orthogonal to the one direction is in a predetermined range and is changed in this range at the time of switching the contents or moving the displayed position in the one direction.

16. The measuring method according to claim 1, wherein the showing display information on the display screen includes adjusting at least one of the reference position and the displayed position as seen from the subject, with a use of an optical system provided between the display screen and the eyeball.

17. The measuring method according to claim 16, wherein the optical system includes at least one prism.

18. The measuring method according to claim 17, wherein the displayed position of the display information in the display screen is adjusted in accordance with refractive characteristics of the prism.

19. The measuring method according to claim 1, wherein the judging whether the subject can recognize the contents of the display information includes determining whether a response to the contents of the display information by the subject coincides with the contents.

20. A designing method for a progressive power lens suitable for rotation characteristics of an eyeball of a subject, the progressive power lens having regions of a distance vision part for distance viewing, a near vision part for near viewing, and an intermediate vision part positioned between the distance vision part and the near vision part, the progressive power lens changing in refractive power between the distance vision part and the near vision part, the designing method comprising:
  measuring the rotation characteristics of the eyeball of the subject according to the measuring method of claim 1;
  adjusting timing to switch the displayed positions and the contents so that at least one of two pieces of information is obtained as the rotation characteristics of the eyeball, the one of the two pieces of information being a limit angle of a line of sight directed to a lowest side relative to the front line of sight, in a range in which the display information is determined to be able to be recognized by rotating the eyeball downward, the other of the two pieces of information being a time period to maintain the eyeball in a state in which the display information is determined to be able to be recognized while the line of sight is directed downward by a predetermined angle relative to the front line of sight; and
  determining a progressive corridor length or a shape of a refractive power curve along which refractive power changes, in the progressive power lens, on a basis of the measured information of the limit angle of the line of sight or the measured information of the time period to maintain the eyeball.

* * * * *